(12) United States Patent
Duffy et al.

(10) Patent No.: US 8,372,054 B2
(45) Date of Patent: Feb. 12, 2013

(54) OVER-THE-WIRE BALLOON CATHETER FOR EFFICIENT TARGETED CELL DELIVERY

(75) Inventors: Angela Duffy, Rahoon (IE); Padraic Curran, Windsor, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 594 days.

(21) Appl. No.: 12/606,481

(22) Filed: Oct. 27, 2009

(65) Prior Publication Data

US 2011/0098671 A1 Apr. 28, 2011

(51) Int. Cl.
*A61M 31/00* (2006.01)
(52) U.S. Cl. .............. 604/509; 604/96.01; 604/101.03; 604/103.01; 604/103.02; 604/500; 604/508; 604/522
(58) Field of Classification Search .............. 604/96.01, 604/101.03, 103.01, 103.02, 500, 508, 509, 604/522
See application file for complete search history.

(56) References Cited

U.S. PATENT DOCUMENTS

| | | | | |
|---|---|---|---|---|
| 4,824,436 A | * | 4/1989 | Wolinsky | 604/509 |
| 5,261,879 A | * | 11/1993 | Brill | 604/96.01 |
| 5,599,307 A | * | 2/1997 | Bacher et al. | 604/101.05 |
| 5,713,917 A | * | 2/1998 | Leonhardt et al. | 606/194 |
| 6,133,502 A | * | 10/2000 | Kasuga et al. | 800/14 |
| 6,932,804 B2 | * | 8/2005 | Lee | 604/506 |
| 7,452,532 B2 | | 11/2008 | Alt | |
| 7,732,190 B2 | * | 6/2010 | Michal et al. | 435/283.1 |
| 7,819,856 B2 | * | 10/2010 | Bates | 604/522 |
| 2006/0074399 A1 | | 4/2006 | Bates | |

OTHER PUBLICATIONS

Sherman, Warren et al., "Catheter-Based Delivery of Cells to the Heart" Nature Clinical Practice Cardiovascular Medicine, Mar. 2006, vol. 3, Supplement 1, pp. S57-S64.

* cited by examiner

*Primary Examiner* — Bhisma Mehta
*Assistant Examiner* — Larry R Wilson

(57) ABSTRACT

A method for delivering a therapeutic substance to a treatment site within a body lumen includes advancing a balloon catheter to the treatment site. A balloon of the balloon catheter is inflated and while the balloon is inflated, a primer that coats the treatment site and attracts the therapeutic substance thereto is delivered through a first fluid delivery lumen of the balloon catheter. The balloon of the balloon catheter is deflated for a predetermined period of time. The balloon of the balloon catheter is reinflated and while the balloon is reinflated, the therapeutic substance is delivered through a second fluid delivery lumen of the balloon catheter. The primer improves adherence of the therapeutic substance to the treatment site.

22 Claims, 5 Drawing Sheets

OVER-THE-WIRE BALLOON CATHETER FOR EFFICIENT TARGETED CELL DELIVERY

FIELD OF THE INVENTION

The invention relates generally to balloon catheters and more particularly to a balloon catheter for delivering a therapeutic substance to a body lumen.

BACKGROUND OF THE INVENTION

The field of cell replacement research and tissue engineering currently is one of the major focuses of medical technology. Cell therapy holds great promise for the future, particularly for degenerative diseases including for example heart failure, diabetes, and spinal cord injury. Loss of cells in organs with low regenerative capacity is critical to repair and recovery of function of that organ.

An exciting area of tissue engineering is the emerging technology of "self-cell" or autologous cell therapy, where cells of a given tissue type are removed from a patient, isolated, perhaps mitotically expanded and/or genetically engineered, and ultimately reintroduced into the donor/patient with or without synthetic materials or other carrier matrices. One goal of autologous cell therapy is to help guide and direct the rapid and specific repair or regeneration of tissues. Such autologous cell therapy is already a part of clinical practice; for example, using autologous bone marrow transplants for various hematologic conditions. One of the greatest advantages of autologous cell therapy over current technologies is that the autologous nature of the tissue or cell greatly reduces, if not eliminates, immunological rejection and the costs associated therewith.

In addition, allogenic cell therapy is also under investigation for tissue repair or regeneration. The term 'allogenic cell' refers to a cell that is isolated from a donor and transplanted into a different individual/non-donor. Allogenic cell therapy is sometimes referred to as 'off-the-shelf' therapy, with companies collecting cells from one or more donors, expanding the cells and packaging them for delivery to patients who were not cell donors. The issue of immunological rejection of allogenic cells can be overcome by isolating, expanding and transplanting specific cell types which have been shown to elicit little or no immune response (e.g. mesenchymal cells).

Thus, there has been interest in the delivery of cells to locations within mammalian bodies to effect new growth of tissue in the region of implantation. Various types of tissue may be implanted, including for example, bone, cartilage, muscle and other types. Similar advances are being made with other tissues such as the liver, the pancreas, tendons and ligaments. Cardiac tissue has also been the subject of cell delivery efforts in order to repair regions severely damaged by myocardial infarctions or congestive heart failure. One example of such use includes stem cells delivered surgically into the myocardium of the patient to regenerate damaged tissue, promote revascularization and angiogenesis. Desired volume concentrations of cells per delivery vary according to indications, but it is not uncommon to have tens to hundreds of millions of cells intended to be delivered to one or more sites.

However, a limitation of cell therapy, particularly within the myocardium, is lack of retention of sufficient numbers of delivered cells at the target site. The present invention is directed to a device and method for cell delivery that improves retention of the cells in the vicinity of the luminal wall.

BRIEF SUMMARY OF THE INVENTION

In an embodiment hereof, a method of delivering a therapeutic substance to a treatment site includes advancing a balloon catheter to the treatment site. A balloon of the balloon catheter is inflated and while the balloon is inflated, a primer that coats the treatment site and attracts the therapeutic substance thereto is delivered through a first lumen of the balloon catheter. The balloon of the balloon catheter is deflated for a predetermined period of time. The balloon of the balloon catheter is reinflated and while the balloon is reinflated, the therapeutic substance is delivered through a second lumen of the balloon catheter. The primer improves adherence of the therapeutic substance to the treatment site. In one embodiment, the therapeutic substance includes cells and the primer is a solution containing one or more cell attractant molecules.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of blood vessels such as the coronary, carotid and renal arteries, the invention may be used in any other body passageways where it is deemed useful and may also be used to treat other body tissues via access through body passageways. Furthermore, there is no intention to be bound by any expressed or implied theory presented in the preceding technical field, background, brief summary or the following detailed description.

Figure 1:
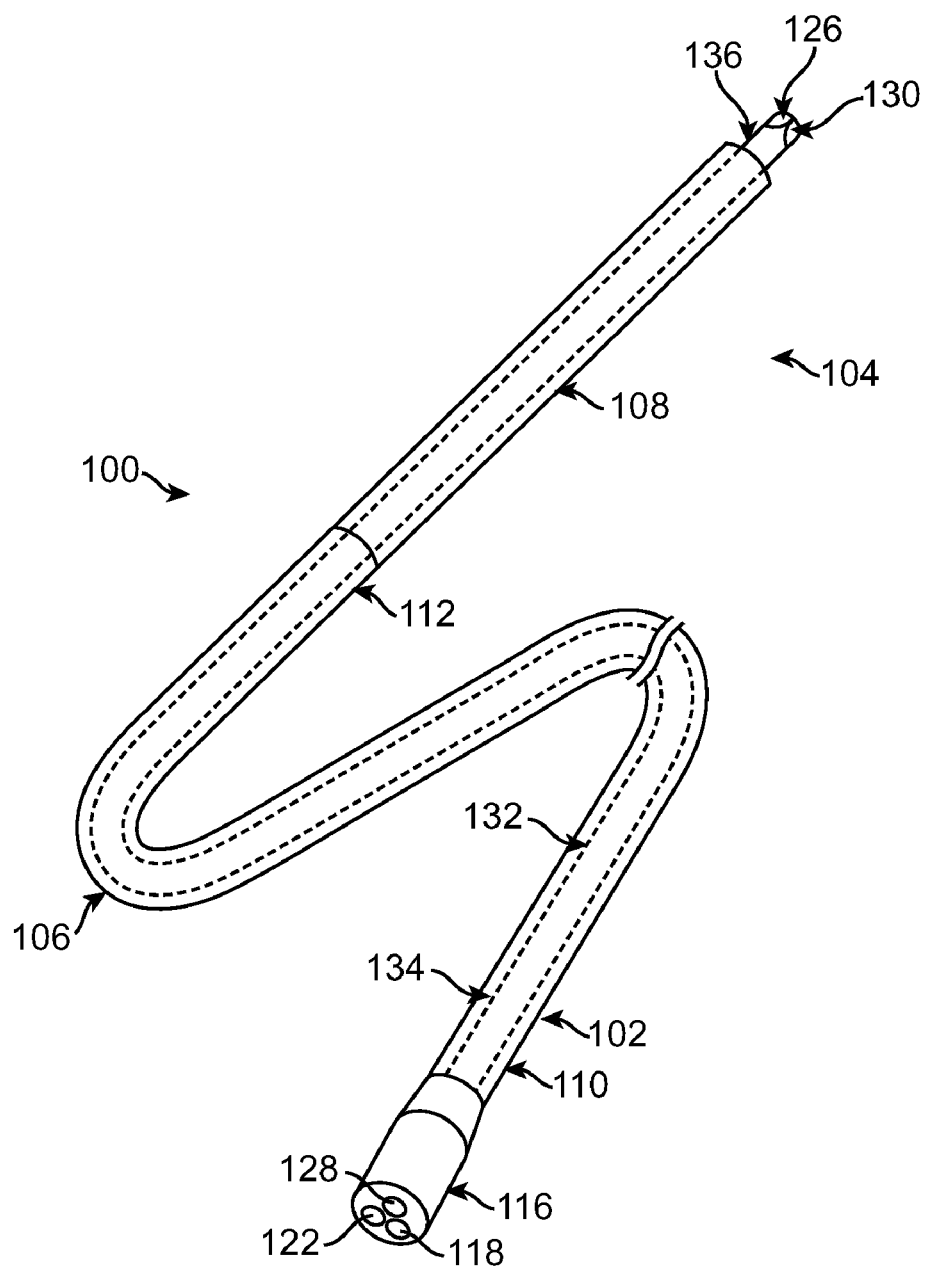
FIG. 1 is a side perspective view of a balloon catheter, wherein the balloon is in an unexpanded configuration, in accordance with an embodiment hereof.
Figure 2:
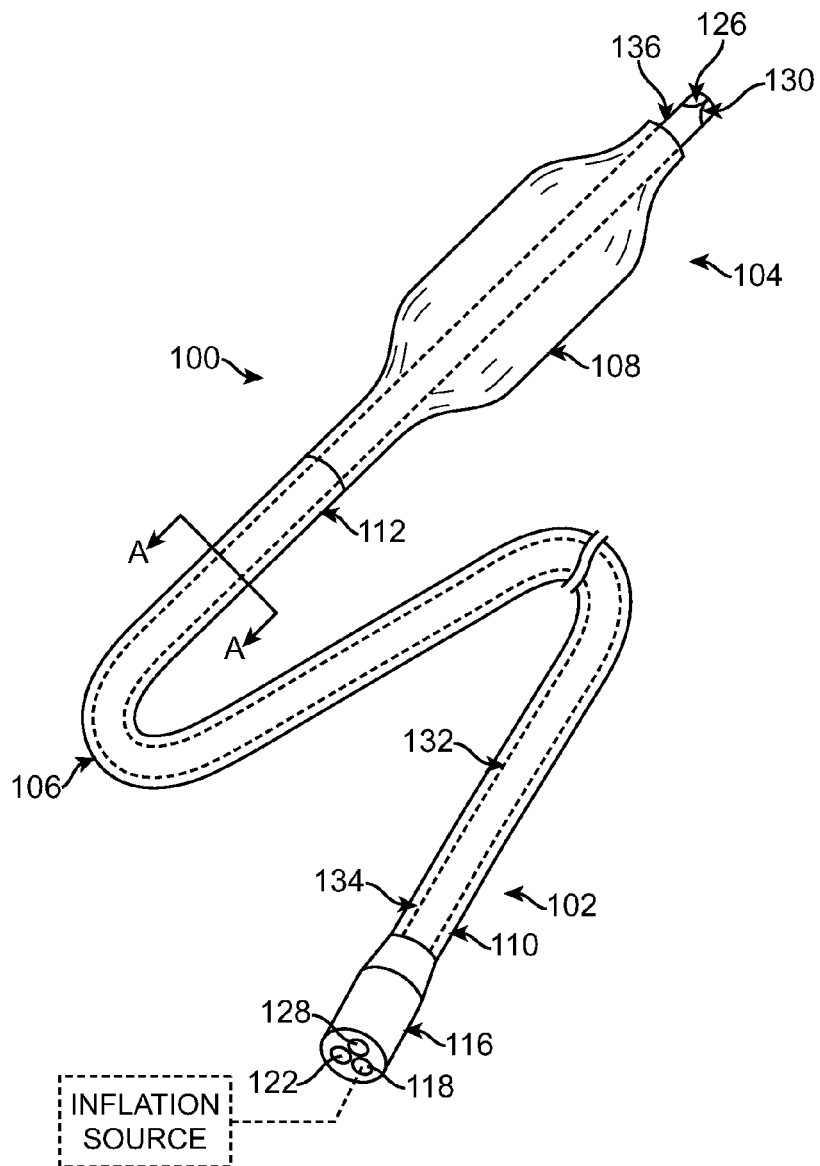
FIG. 2 is a side perspective view of the balloon catheter of FIG. 1, wherein the balloon is in an expanded configuration.

FIGS. 1 and 2 depict a balloon catheter 100 according to an embodiment hereof. Balloon catheter 100 includes a proximal portion 102 that extends out of the patient and has a hub 116. Distal portion 104 of catheter 100 is positionable at a target location within the vasculature and includes an inflatable balloon 108 mounted thereon, which is shown in an unexpanded or delivery configuration in FIG. 1 and in an expanded or inflated configuration in FIG. 2. Catheter 100 may be used to deliver a therapeutic substance into a body lumen. In one embodiment, catheter 100 may be used to deliver cells to the walls and interior of a body vessel and/or to the tissue adjacent to the body vessel. In addition, delivery of the therapeutic substance may be carried out at the same time as a revascularization procedure. Thus, catheter 100 may be used in balloon angioplasty procedures, and may form the basis of a stent delivery system and/or a graft delivery system.

Figure 2A:
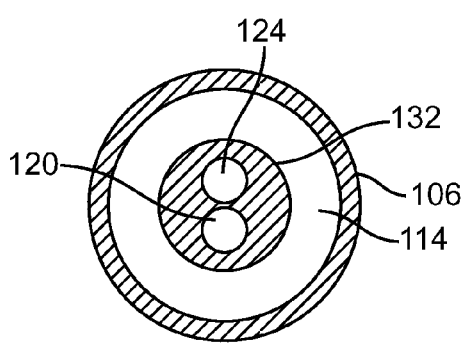
FIG. 2A is a cross-sectional view taken along line A-A of FIG. 2.

In one embodiment illustrated in FIG. 2A, balloon catheter 100 has an over-the-wire (OTW) coaxial catheter configuration with an outer tubular component or shaft 106 and a dual lumen inner shaft 132. Outer shaft 106 has a proximal end 110 coupled to a hub 116 and a distal end 112 coupled to a proximal end of balloon 108. Inner shaft 132 has a proximal end 134 coupled to hub 116 and a distal end 136 terminating distally of balloon 108. Inner shaft 132 extends coaxially within outer shaft 106 such that an annular inflation lumen 114 is defined between an inner surface of outer shaft 106 and an outer surface of inner shaft 132. Inflation lumen 114 thus extends between proximal and distal ends 110, 112 of outer catheter shaft 106 and into the inner volume of balloon 108 to allow inflation fluid received through an inflation port 118 of hub 116 to be delivered to balloon 108. A distal end of balloon 108 is coupled to inner shaft 132. As will be explained in more detail herein, balloon 108 is inflated during delivery of a therapeutic substance and delivery of a primer that increases adherence of the therapeutic substance to the luminal wall. Prolonged balloon inflation is generally not desirable because balloon 108 in the expanded configuration blocks blood flow within the vessel, thus blocking oxygen flow therethrough as well. Thus, multiple short-term balloon inflations and deflations are used to allow the administered therapeutic substance to adhere to the luminal wall. As would be understood by one of ordinary skill in the art of balloon catheter design, hub 116 provides a luer hub or other type of fitting that may be connected to a source of inflation fluid and may be of another construction or configuration without departing from the scope of the present invention.

Inner shaft 132 defines two separate lumens, a first fluid delivery lumen 120 and a second fluid delivery lumen 124, extending parallel or side-by-side to each other for the length of inner shaft 132. Although depicted as circular in cross-section, one or more lumen(s) of inner shaft 132 may have any suitable cross-section including for example circular, elliptical, or crescent-shaped. The distal ends of first and second lumens 120, 124 are open and define distal ports 126, 130, respectively. First lumen 120 accommodates a guidewire received through a first proximal port 122 of hub 116 and also serves to deliver a therapeutic agent through distal port 126 after removal of the guidewire. Second lumen 124 serves as a passageway to deliver a primer that coats the treatment site and attracts the therapeutic substance thereto, thus increasing adherence of the therapeutic substance to a luminal wall. The primer is received through a proximal fluid delivery port 128 of hub 116 and delivered through distal port 130 prior to delivery of the therapeutic substance. As such, catheter 100 may be utilized to efficiently target and improve adherence of a therapeutic substance to an injury site. Dual lumen inner shaft 132 allows the therapeutic substance and primer to be delivered through separate lumens in order to prevent the therapeutic substance from adhering within catheter 100. Since the guidewire may be removed at any point in the procedure after balloon catheter 100 is in place at the treatment site as desired, second lumen 124 may alternatively be utilized for accommodating a guidewire without departing from the scope of the present invention.

In one embodiment, the therapeutic substance includes stem cells. The term "stem cells" refers to a cell that has the potential to regenerate tissue over a lifetime. Stem cells have the ability to renew themselves through numerous cycles of mitotic cell division while maintaining the undifferentiated state, and have the capacity to differentiate into a diverse range of specialized cell types. In a developing embryo, stem cells can differentiate into all of the specialized embryonic tissues. In adult organisms, stem cells and progenitor cells act as a repair system for the body, replenishing specialized cells, but also maintain the normal turnover of regenerative organs, such as blood, skin or intestinal tissues.

The primer is a solution containing a sufficient concentration of one or more cell attractant molecules, such as, but not limited to, chemokines, ligands such as CXC-chemokine stromal cell-derived factor-1 (SDF-1) or monocyte chemotactic protein-1 (MCP-1), or antibodies such as STRO-1, or antibodies binding CD34, CD44, CD133, ABCG2, Sca-1, Stem cell factor (SCF)/c-Kit ligand, Bone morphogenetic protein receptor (BMPR), Colony-forming unit (CFU), Lineage surface antigen (Lin), Thy-1, Oct-4/POU5F1, Stage Specific Embryonic Antigens (SSEA-1, -3 and -4), Alkaline phosphatase, Cluster designation 30 (CD30), Cripto (TDGF-1), GCTM-2, Genesis, Germ cell nuclear factor, TRA-1-60, TRA-1-81, Vimentin, Nestin, PSA-NCAM (Polysialic acid-neural cell adhesion molecule) or p75 Neurotrophin R (NTR). In another embodiment, the therapeutic substance is cells and the primer is suitable for long-term treatment including multiple follow-up cell administrations, local or systemic, over the course of months or years. For example, the long-term primer may be a viral or non-viral gene delivery vector housing a chemo-attractant gene(s).

In another embodiment, a biopolymer scaffold used in conjunction with cells can enhance cell viability, improve angiogenesis, and improve cardiac function. For example, biopolymers such as fibrin, collagen, and matrigel can be delivered to the target location with the cells. In a non-limiting example, fibrin glue used with bone marrow derived cells or cells from the endothelial lineage in the myocardium provides superior results than cells alone. However, fibrin glue is viscous and therefore difficult to deliver through a conventional single lumen catheter. The dual lumen catheter of the present invention can be used with components of fibrin to deliver cells to a target location in a fibrin scaffold. In particular, fibrin glue comprises fibrinogen monomers and thrombin. Exposure of the fibrinogen to thrombin converts the fibrinogen to fibrin, which polymerizes to form a fibrin mesh. Thus, the selected cells can be mixed with the fibrinogen solution or the thrombin solution or both. The solutions are delivered separately through lumens 120, 124 to the target location. At the target location, the fibrinogen and thrombin are exposed to each other to form the fibrin mesh.

Inner and outer catheter shafts 106, 132 may be formed of a polymeric material, non-exhaustive examples of which include polyethylene, PEBA, polyamide and/or combinations thereof, either blended or co-extruded. Optionally, the catheter shafts or some portion thereof may be formed as a composite having a reinforcement material incorporated within a polymeric body in order to enhance strength and/or flexibility. Suitable reinforcement layers include braiding, wire mesh layers, embedded axial wires, embedded helical or circumferential wires, and the like. In one embodiment, for example, at least a proximal portion of outer catheter shaft 106 may be formed from a reinforced polymeric tube.

Figure 2B:
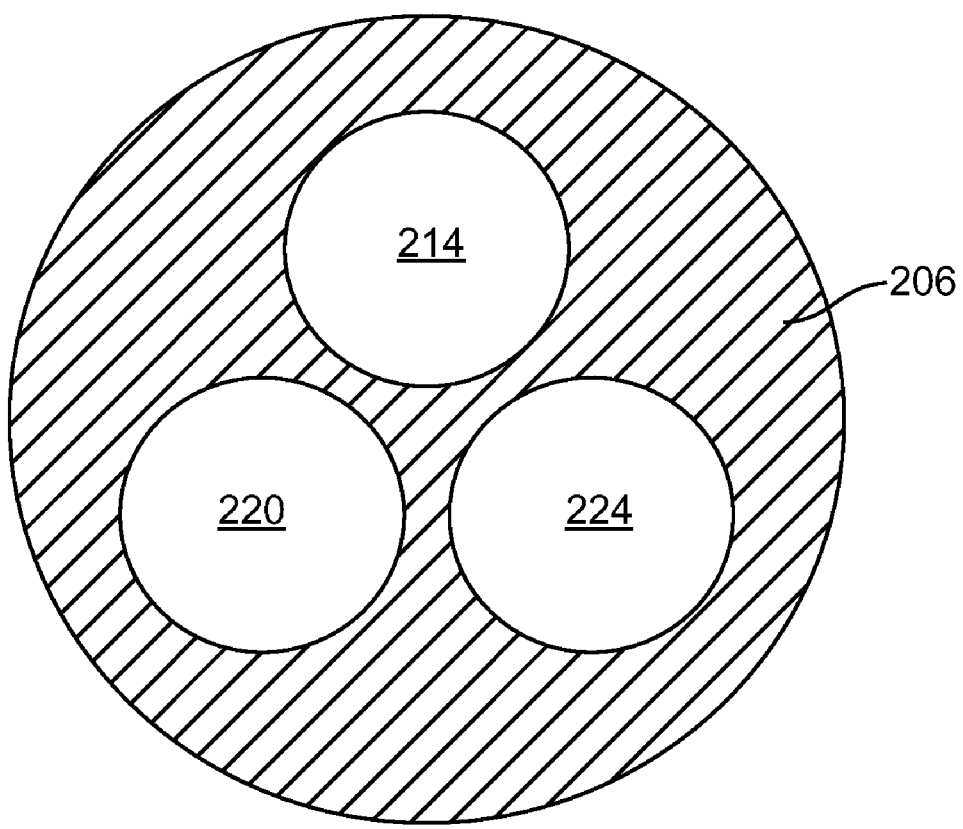
FIG. 2B is a cross-sectional view according to an alternate embodiment hereof.

Other types of catheter construction are also amendable to the invention, such as, without limitation thereto, a catheter shaft formed by multi-lumen profile extrusion. For example, an alternate catheter construction is illustrated in FIG. 2B. Rather than including coaxial inner and outer catheter shafts, a single catheter shaft 206 may define an inflation lumen 214, a first lumen 220, and a second lumen 224, each extending substantially the entire length of the catheter and parallel to each other. Although depicted as circular in cross-section, one or more lumen(s) of shaft 206 may have any suitable cross-section including for example circular, elliptical, or crescent-shaped. Catheter shaft 206 includes one or more ports or passageways (not shown) formed therein such that inflation lumen 214 is in fluid communication with the interior volume of balloon 108.

Figure 3:
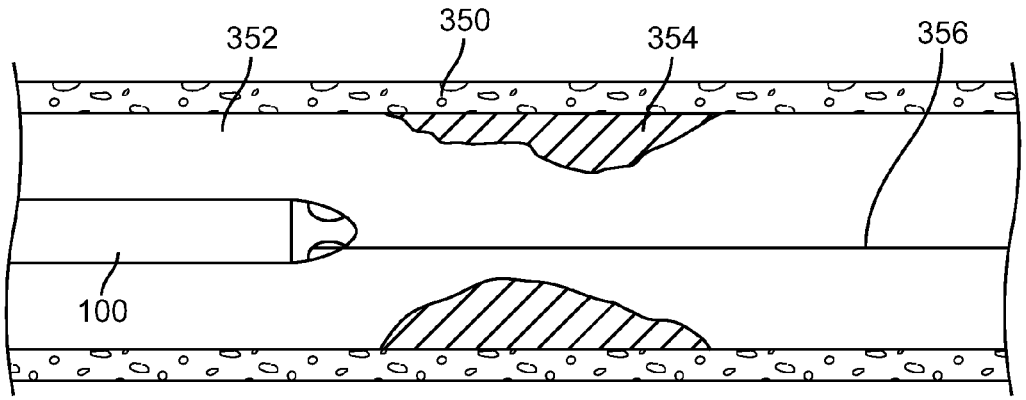
FIGS. 3-8 illustrate the steps of a method of delivering a therapeutic substance within a body lumen of a vessel according to an embodiment hereof.

FIGS. 3-8 illustrate the steps of a method of delivering a therapeutic substance within a body lumen 352 of a vessel 350 according to an embodiment hereof. Although described in relation to delivering a therapeutic substance during a revascularization procedure, it should be understood that the methods and apparatus described herein may be used to only deliver a therapeutic substance. Further, although described as advancing a balloon catheter over a previously positioned guidewire, it should be understood that the balloon catheter and guidewire may be simultaneously advanced to and through the target lesion. Typically, a guiding catheter is first inserted through an incision (not shown) and into a femoral artery of a patient. A guidewire 356 is maneuvered through the vasculature to a treatment site, which in this instance is shown as a lesion 354 within body lumen 352 of vessel 350. As shown in FIG. 3, catheter 100 is delivered by a clinician by threading catheter 100 over guidewire 356 through the first lumen of the dual lumen inner shaft through the vascular system of the patient.

Figure 4:
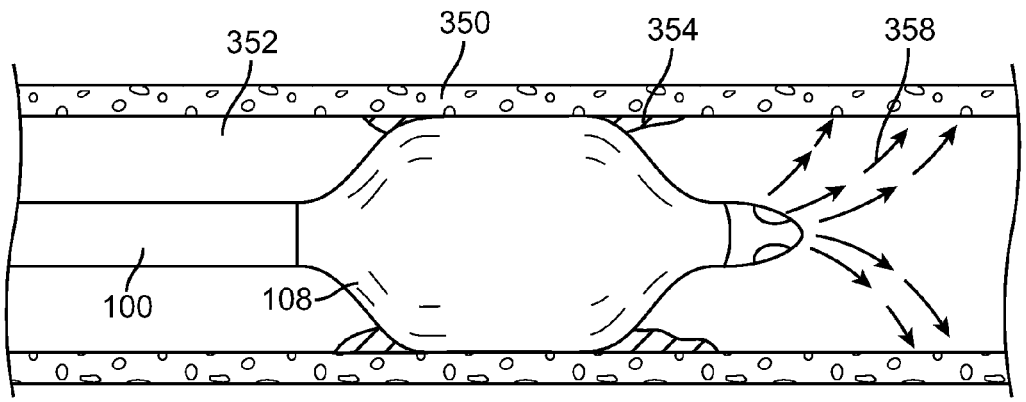

Once catheter 100 is positioned as desired (i.e., balloon 108 is positioned within lesion 354), removal of guidewire 356 may occur at any time prior to delivery of a therapeutic substance. Inflation fluid is introduced into the inflation lumen of catheter 100 to expand balloon 108 within the narrowed body lumen 352 to dilate vessel 350 as shown in FIG. 4. The angioplasty procedure thus restores adequate blood flow through the affected vessel 350 by balloon inflation. A primer (represented by arrows 358) is delivered through the second lumen of catheter 100 and allowed to coat the luminal wall of vessel 350 for a predetermined period of time while balloon 108 is inflated. In one embodiment, the predetermined period of time is between 3-4 minutes since balloon 108 in the expanded configuration blocks blood flow within the vessel and prolonged blockage is generally not desirable. However, in another embodiment, the predetermined period of time may be greater than four minutes (i.e., up to twenty minutes) in order to ensure that the primer completely coats the luminal wall. In yet another embodiment, the predetermined period of time may be less than three minutes as long as at least a portion of the delivered primer coats the luminal wall of the treatment site.

Figure 5:
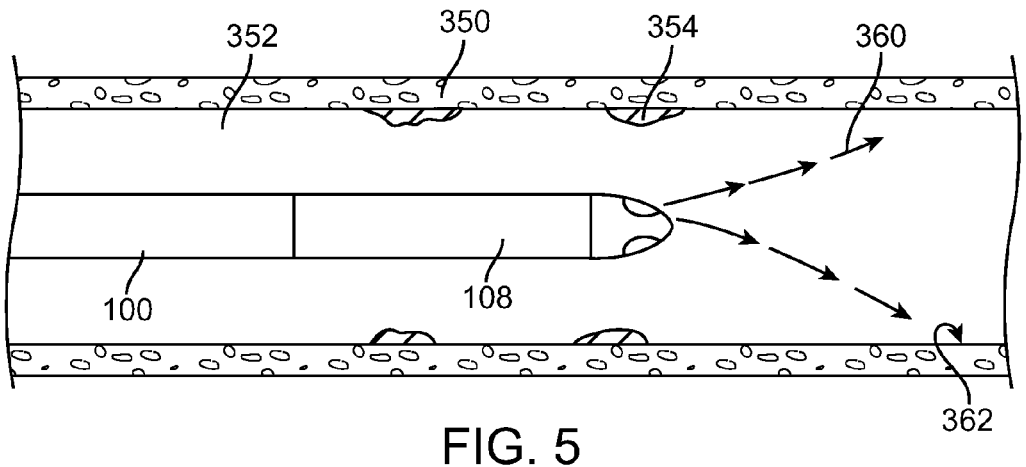

Referring now to FIG. 5, balloon 108 is then deflated and any excess primer remaining in the second lumen of catheter 100 may be washed away by flushing saline or other suitable solution (represented by arrows 360) there through. As a result of this flushing step, any excess primer is advanced downstream into vessel 350 and may coat distal luminal areas 362. Advantageously, any excess therapeutic substance that is subsequently flushed downstream will adhere to distal luminal areas 362 coated with primer.

Figure 6:
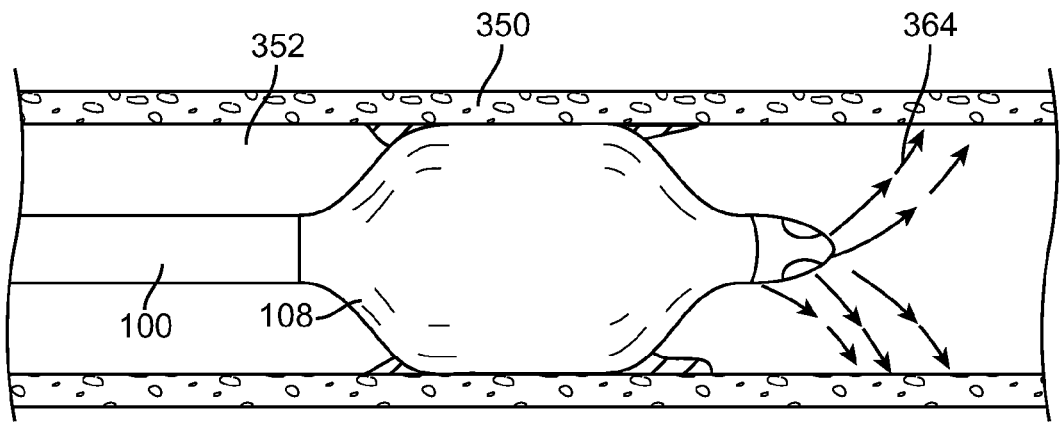

After a predetermined period of time, such as approximately four minutes, balloon 108 of catheter 100 is then re-inflated and a therapeutic substance such as cells (represented by arrows 364) are delivered through the first lumen of catheter 100 as shown in FIG. 6. A predetermined period of time is allowed for adherence of the cells to the primer. In one embodiment, the predetermined period of time is between 3-4 minutes since balloon 108 in the expanded configuration blocks blood flow within the vessel and prolonged blockage is generally not desirable. However, in another embodiment, the predetermined period of time may be greater than four minutes (i.e., up to twenty minutes) in order to ensure that the cells completely adhere to the primer. In yet another embodiment, the predetermined period of time may be less than three minutes as long as at least a portion of the delivered cells coat the luminal wall of the treatment site.

Figure 7:
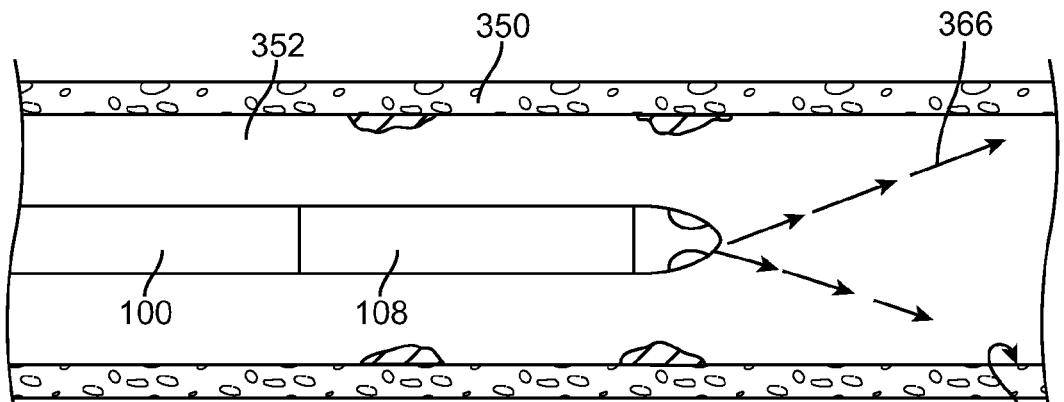
Figure 8:
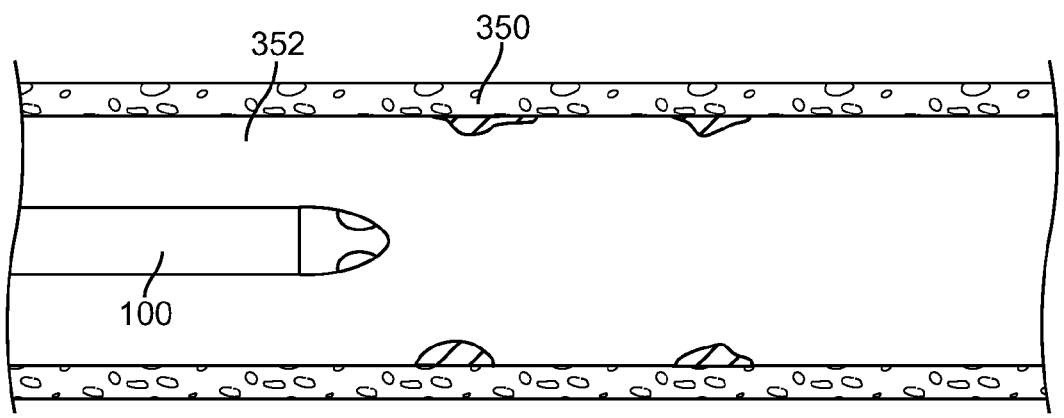

Balloon 108 may then by deflated and any excess cells remaining in the first lumen of catheter 100 may be washed away by flushing saline or other suitable solution (represented by arrows 366) there through as shown in FIG. 7. As a result of this flushing step, any excess cells are advanced downstream into vessel 350 and will adhere to distal luminal areas 362 coated with primer. In the deflated position as shown in FIG. 8, catheter 100 may be withdrawn and removed from the patient, leaving the delivered cells adhering to the luminal wall of vessel 350 for treatment thereof.

Although the steps described above deliver the primer and therapeutic substance at separate times through the separate lumens, different solutions may be delivered through the first and second lumens simultaneously to be exposed to each other at the target location. For example, the catheter may be delivered to the target location as described with respect to FIG. 3. Depending on the application, the balloon may be inflated as described with respect to FIG. 4. A first solution may then be delivered through the first lumen simultaneously with a second solution delivered through the second lumen. The first and second solutions exit the catheter simultaneously and mix together. For example, the first solution may include fibrinogen and the second solution may include thrombin. The fibrinogen solution and thrombin solution are delivered separately through the catheter to the target location. At the target location, the fibrinogen and thrombin solutions mix to form a fibrin scaffold. Cells or other therapeutic substances may be contained in the fibrinogen or thrombin solutions or both to be delivered to the target location.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of delivering a therapeutic substance to a treatment site within a body lumen, the method comprising the steps of:

advancing a balloon catheter to the treatment site;

inflating a balloon of the balloon catheter at the treatment site;
delivering a primer through the balloon catheter while the balloon is inflated, wherein the primer is a solution that coats the treatment site and attracts the therapeutic substance thereto;
deflating the balloon of the balloon catheter after the step of delivering the primer through the balloon catheter;
reinflating the balloon of the balloon catheter after the step of deflating the balloon; and
delivering the therapeutic substance through the balloon catheter while the balloon is reinflated, wherein the primer improves adherence of the therapeutic substance to the treatment site.

2. The method of claim 1, wherein the treatment site includes a lesion.

3. The method of claim 1, wherein the step of delivering a primer includes allowing the primer to coat the luminal wall of the body lumen for a predetermined amount of time less than twenty minutes.

4. The method of claim 3, wherein the predetermined amount of time is between three and four minutes.

5. The method of claim 1, further comprising the step of flushing any excess primer remaining in the catheter after the step of delivering the primer.

6. The method of claim 5, further comprising the step of flushing any excess therapeutic substance remaining in the catheter after the step of delivering the therapeutic substance.

7. The method of claim 1, wherein the balloon catheter includes an inflation lumen, a first fluid delivery lumen and a second fluid delivery lumen.

8. The method of claim 7, wherein the step of delivering a primer occurs through the first fluid delivery lumen and the step of delivering the therapeutic substance occurs through the second fluid delivery lumen.

9. The method of claim 7, wherein the balloon catheter includes an outer shaft and an inner shaft extending coaxially within the outer shaft, wherein the inflation lumen is defined between an outside surface of the inner shaft and an inside surface of the outer shaft, and wherein the first fluid delivery lumen and the second fluid delivery lumen are disposed within the inner shaft.

10. The method of claim 7, wherein the step of advancing the balloon catheter to the treatment site includes advancing the balloon catheter over a guidewire disposed in the first fluid delivery lumen or the second fluid delivery lumen.

11. The method of claim 1, wherein the therapeutic substance includes cells.

12. The method of claim 11, wherein the primer is a solution containing one or more cell attractant molecules.

13. The method of claim 12, wherein the one or more cell attractant molecules is selected from the group consisting of chemokines, ligands, and antigens binding CD34 and CD44 receptors.

14. The method of claim 12, wherein the primer is a gene delivery vector housing one or more chemo-attractant genes.

15. A method of delivering cells to a treatment site, the method comprising the steps of:
advancing a balloon catheter over a guidewire to the treatment site, wherein the balloon catheter defines a first fluid delivery lumen and a second fluid delivery lumen each extending substantially the entire length of the catheter;
inflating a balloon of the balloon catheter at the treatment site;
delivering a primer through the second fluid delivery lumen of the balloon catheter while the balloon is inflated, wherein the primer is a solution containing one or more cell attractant molecules;
deflating the balloon of the balloon catheter after the step of delivering the primer through the balloon catheter;
reinflating the balloon of the balloon catheter after the step of deflating the balloon; and
delivering the cells through the first fluid delivery lumen of the balloon catheter while the balloon is reinflated, wherein the primer improves adherence of the cells to the treatment site.

16. The method of claim 15, wherein the one or more cell attractant molecules is selected from the group consisting of chemokines, ligands, and antigens binding CD34 and CD44 receptors.

17. The method of claim 15, wherein the primer is a gene delivery vector housing one or more chemo-attractant genes.

18. The method of claim 15, wherein the step of delivering a primer includes allowing the primer to coat the luminal wall of the treatment site for a predetermined amount of time less than twenty minutes.

19. The method of claim 18, wherein the predetermined amount of time is between three and four minutes.

20. The method of claim 15, further comprising the steps of flushing any excess primer remaining in the second fluid delivery lumen through the catheter after the step of delivering the primer and subsequently flushing any excess cells remaining in the first fluid delivery lumen through the catheter after the step of delivering the cells.

21. The method of claim 15, wherein the treatment site includes a lesion.

22. The method of claim 15, wherein the balloon catheter is advanced over a guidewire disposed through the first fluid delivery lumen or the second fluid delivery lumen and the method further comprises the step of removing the guidewire prior to the step of delivering the cells or prior to the step of delivering the primer.

* * * * *